US006204670B1

United States Patent
Joshi

(10) Patent No.: US 6,204,670 B1
(45) Date of Patent: Mar. 20, 2001

(54) PROCESS AND INSTRUMENT FOR MOISTURE MEASUREMENT

(75) Inventor: Kalpana Keshav Joshi, Pune (IN)

(73) Assignee: National Research Development Corp., New Delhi (IN)

( * ) Notice: Subject to any disclaimer, the term of this patent is extended or adjusted under 35 U.S.C. 154(b) by 0 days.

(21) Appl. No.: 09/092,904

(22) Filed: Jun. 8, 1998

(30) Foreign Application Priority Data

Jun. 9, 1997  (IN) .......................................... 350/97
Mar. 25, 1998 (IN) .......................................... 180/98

(51) Int. Cl.[7] .................................................. G01R 27/04
(52) U.S. Cl. ............................................ 324/643; 324/636
(58) Field of Search .................................. 324/633, 643, 324/634, 637, 653, 642, 636

(56) References Cited

U.S. PATENT DOCUMENTS

| | | | |
|---|---|---|---|
| 4,193,027 | 3/1980 | Wyslouzil | 324/58.5 R |
| 4,270,083 * | 5/1981 | Fitzky et al. | 324/58.5 C |
| 4,361,801 * | 11/1982 | Meyer et al. | 324/638 |
| 4,408,128 | 10/1983 | Fujita | 324/65 R |
| 4,674,325 | 6/1987 | Kiyobe et al. | 73/73 |
| 4,991,915 | 2/1991 | Thompson et al. | 324/640 |
| 5,015,954 * | 5/1991 | Dechene et al. | 324/307 |
| 5,039,947 * | 8/1991 | Kraszewski et al. | 324/634 |
| 5,208,544 | 5/1993 | McBrearty et al. | 324/687 |
| 5,315,167 | 5/1994 | Chan et al. | 307/296.6 |
| 5,331,284 * | 7/1994 | Jean et al. | 324/639 |
| 5,376,888 * | 12/1994 | Hood | 324/643 |
| 5,420,517 | 5/1995 | Skaling et al. | 324/643 |
| 5,455,516 * | 10/1995 | Jean et al. | 324/639 |
| 5,646,537 | 7/1997 | Skaling et al. | 324/643 |
| 5,666,061 * | 9/1997 | Assenheim | 324/636 |
| 5,726,578 * | 3/1998 | Hood | 324/643 |

OTHER PUBLICATIONS

Technical Memorandum entitled "Microstrip with Dielectric Overlay: Variational 1994 Analysis and Validation" by K.K. Joshi et al. IEE Proc. Antennas Propag, vol. 141, No. 2, Apr. 1994.

Article entitled "Conductor, Dielectric and Radiation Losses in Multilayer Microstrip Interconnects with Dielectric Cover for High Performance . . . " by K.K. Joshi et al., Dept. of Electronics, S.P. College, Pune, India.

* cited by examiner

*Primary Examiner*—Safet Metjahic
*Assistant Examiner*—Vincent Q Nguyen
(74) *Attorney, Agent, or Firm*—Michael D. Bednarek; Shaw Pittman

(57) ABSTRACT

A process for measuring moisture of grains, fruits, nuts and the like (a sample) by connecting the input of a multilayer microstrip hybrid circuit (MMHC) to a pulse generating source, precalibrating the pulse generating source and a time domain reflectometer and connecting the output of the MMHC to a detector. The time domain reflectometer is then calibrated to obtain a characteristic reference reflection and time of propagation through the MMHC is recorded. The sample is placed on the MMHC and a time delay is measured in response to the characteristic reference reflection. The effective permittivity is then calculated based on the parameters of the time domain reflectometer, time delay, reflection coefficient and characteristic impedance of the MMHC. The calculated effective permittivity is then calibrated against moisture.

3 Claims, 7 Drawing Sheets

Figure 1:
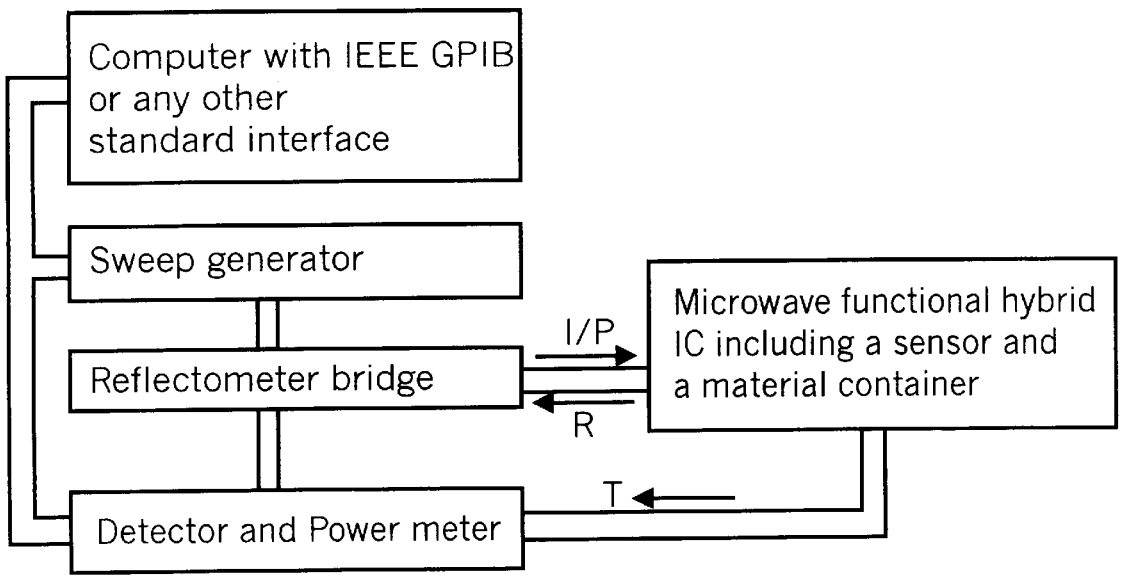
Figure 1:
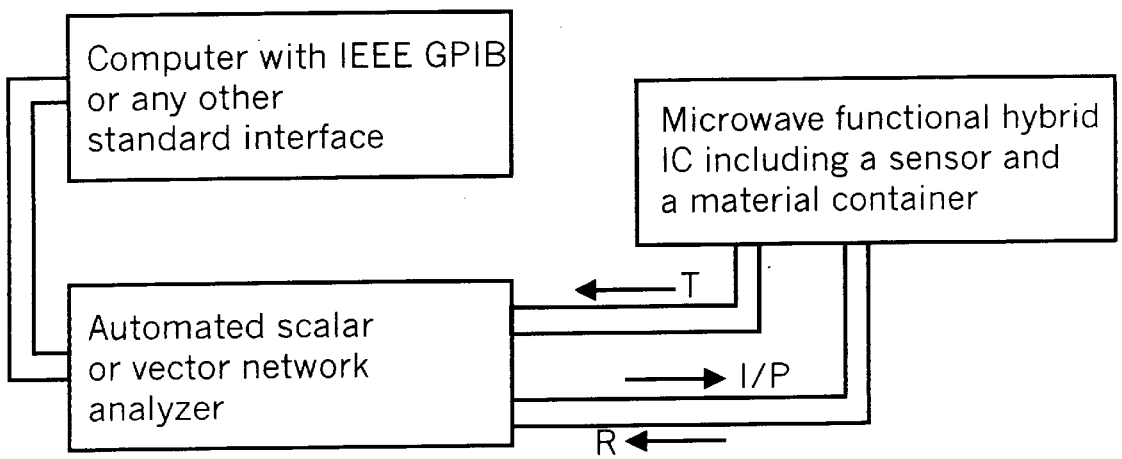

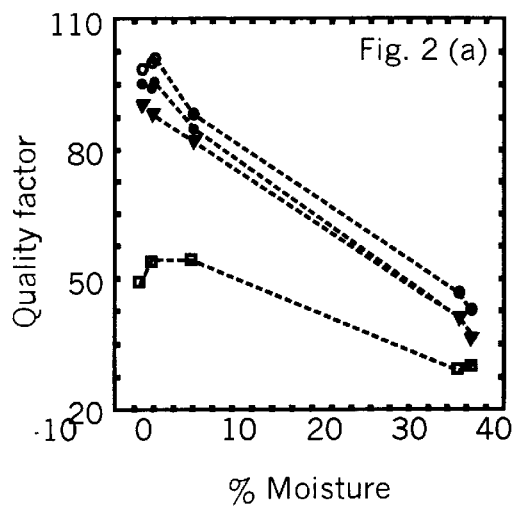
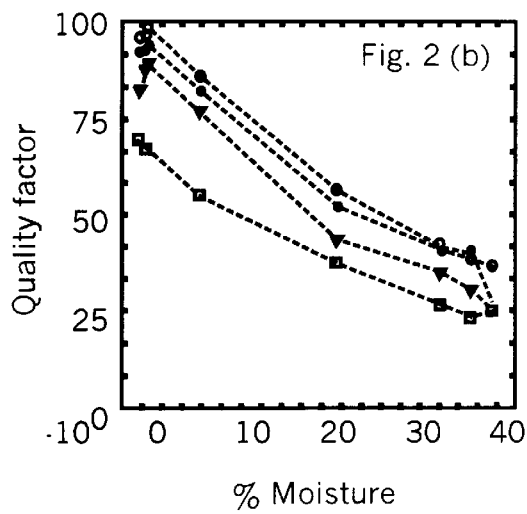
Fig. 2 Variation in Q factor with % moisture in a single wheat grain for four different weight groups and four different orientations (0°, +45°, -45°, 90°)
a) 0.045gm, b) 0.055 gm, c) 0.065 gm, d) 0.075 gm.
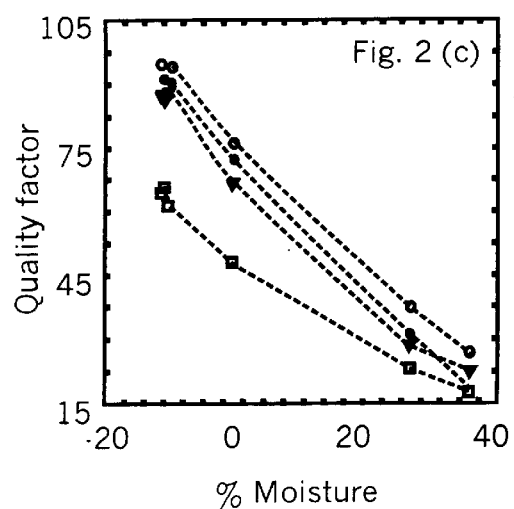
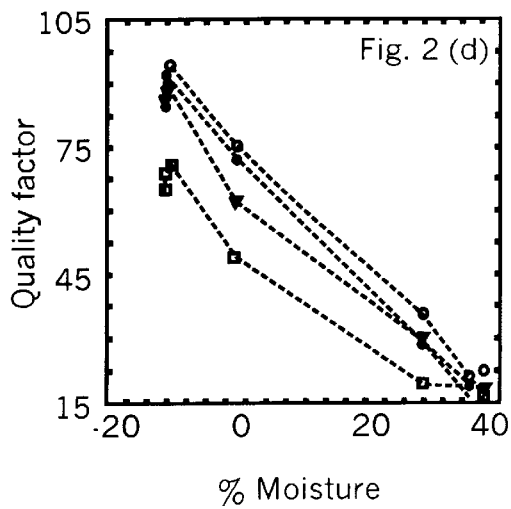

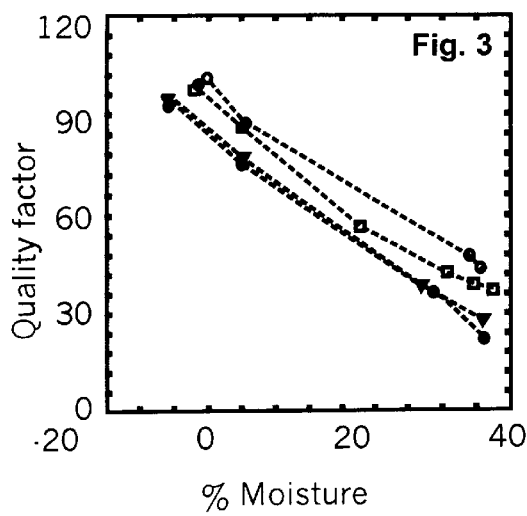

Fig. 3 Variation of Q factor with % moisture in a single wheat grain for four different weight groups at 90° orientation.

Fig. 4 Variation of resonant frequency with % moisture in a single wheat grain for 0.045 gm weight group with four different orientations.

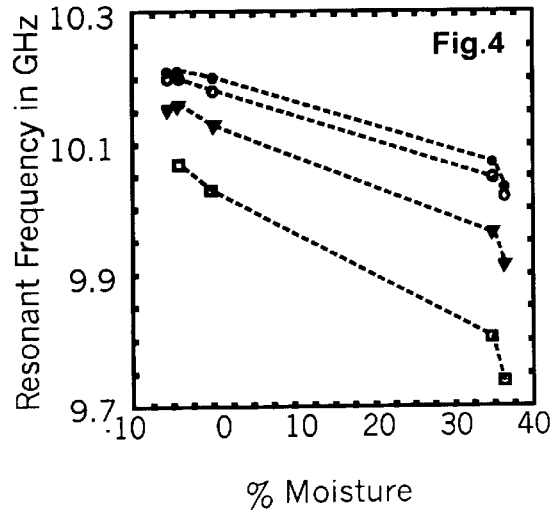

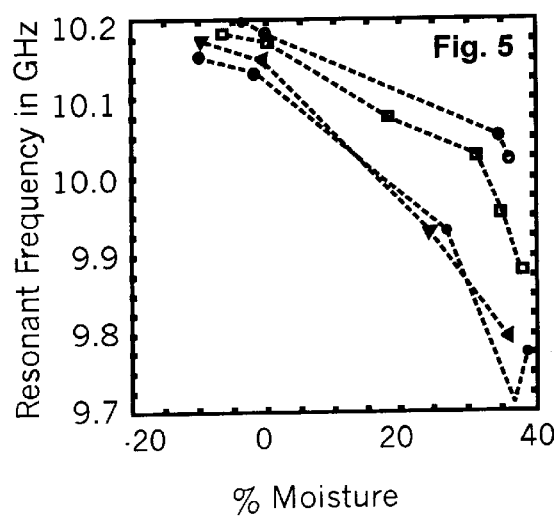

Fig. 5 Variation of resonant frequency with % moisture in a single wheat grain for four different weight groups at 90° orientation.

Cross sectional view

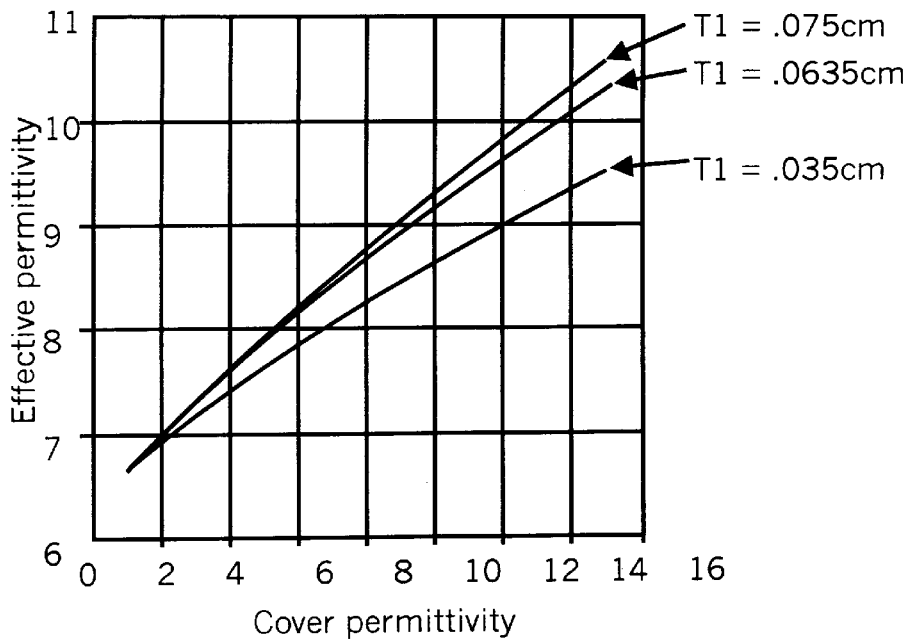
Fig. 14 (a) Variation of effective permittivity with cover permittivity and cover thickness; substrate permittivity = 9.99, h=0.635mm, w=0.620mm, t=0.005mm, T1 = cover thickness
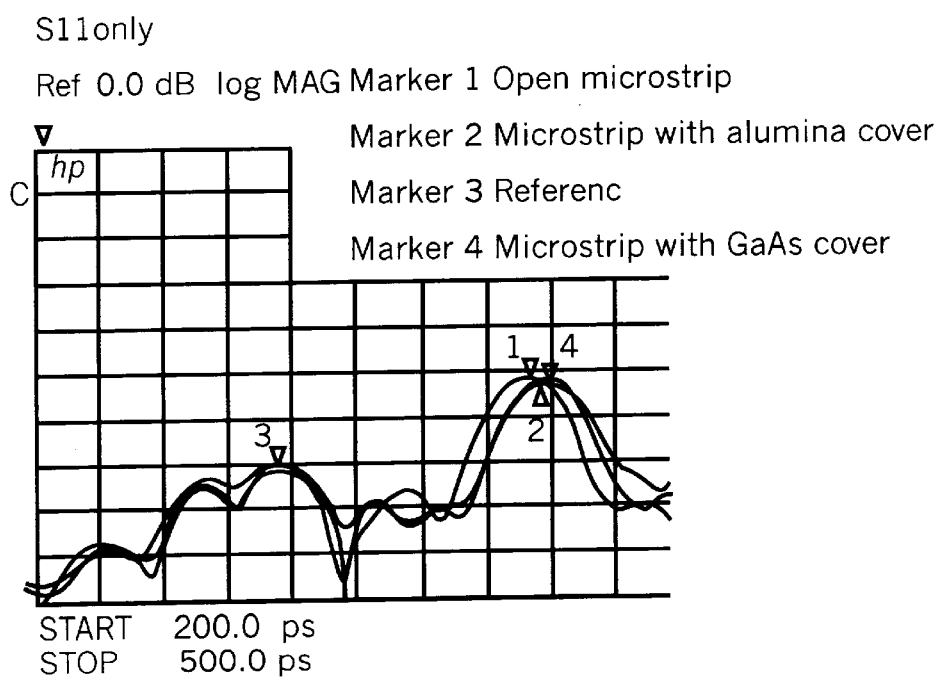
Fig. 14 (b) Frequency shift due to different dielectric covers plotted on HP 8510C Network Analyzer

PROCESS AND INSTRUMENT FOR MOISTURE MEASUREMENT

The present invention relates to a process and an instrument for determining the content of moisture in the articles such as grains, pulverised samples, fruits, nuts and dry fruits and industrial articles as well as food products. More precisely it relates to a moisture sensing instrument which uses the measurement of dielectric properties for quantifying the moisture content of samples working in the range of microwave frequencies.

The present invention relates to an instrument for determining moisture content in solid as well as liquid samples. The instrument for measuring moisture content in liquid as well as solid is a non-destructive moisture sensing instrument which uses dielectric properties and effective microstrip permittivity for measuring the moisture content of samples in Time Domain. The present invention also relates to a process for determining the moisture content in solid and liquid samples and defines the technique used for such measurement.

The instrument of the present invention is employed to measure the moisture content of samples such as soil, paper, fruits, single grains, bulk grains, pulverised industrial and agricultural products like flours, soap/detergent powders, chemical fertilizers. This instrument of the present invention is equally effective in measuring the moisture content of liquids such as sugar syrups; milk products; fruits such as apples, grapes, watermelons; oil based products like margraine.

BACKGROUND OF THE INVENTION

It is essential to determine the moisture content in the articles especially relating to articles used in food industry. The knowledge about the moisture content is essential factor for selecting the storage conditions and the safe storage period of a particular sample. Moisture content of various industrial materials like rubbers, foam, soap cakes, pharmaceutical products is an important factor for storage, shelf life and quality control.

Measurement of dielectric properties is important in the industrial processes involving polymers, rubbers, ceramics and plastics for the quality control as well as correct chemical compositions of the product in the liquid, semisolid or solid state.

Standard gravimetric laboratory tests are tedious and require several hours for completion, also they are destructive in nature. Number of conductivity based and capacitive techniques measure average moisture in bulk materials and need particular size of the sample to be measured. Moisture meters with penetrating probes are suitable for semisolid or grainy material or liquids only. Waveguide resonant cavity techniques have been widely used to perform non-destructive moisture measurements as well as complex permittivities of semiconductor materials. The waveguide cavity technique is associated with various difficulties like loading and unloading of samples even though it is considered as an accurate technique.

Moisture measurements in materials like rubber lining need a sensor which can measure moisture with surface contact only. The present technique can also be used for the measurement of thickness of ice formed on the wings of the aircraft of a space shuttle.

The moisture content of grains, seeds and food products such as wheat, rice, coffee is an important factor for the storage of grain, determination of the time of harvesting, marketing and processing (S. O. Nelson, V. K. Chari Kandala and Kurt C. Lowrence. "Moisture determination in single grain kernels and Nuts by RF Impedance Measurements". IEEE Trans. on Instrumentation and Measurements, Vol 41, No. 6, Dec. 1992 and Andrezej W. Kraszevaski, "Microwave Aquametry—Needs and Perspective," IEEE Trans. on Microwave theory and techniques, Vol 39, No. 5, May 1991)

Moisture measurement is performed on the samples from yields of a cereal or pulse product to correct the yield figure. The error of moisture content of 1% in one ton of yields can cause an error of 10 Kg. Forecasting of the yields is important for enabling to take an action against the unbalanced demand and supply of the cereal products. It is extremely important to store the grain stock only after the moisture contents have been measured to ensure the prevention of insect manifestation. Measurement of moisture of materials is important in several industrial processes such as production of soaps. Similarly moisture measurement for liquids such as fruit products is essential. Measurement of moisture of materials is important in several industrial processes such as production of soaps, powders, biscuits, sugar syrups and for oil based products such as margarine.

The prior art cites references to different methods of quantifying the moisture contents. Moisture meters/sensors have been used which include the standard gravimetric laboratory tests which are tedious and require several hours and days for completion. Conventional electric and electronic moisture meters measure average moisture in bulk grain sample. The average does not provide any information on the range of moisture in the individual grains or seed moisture content [A. W. Kraszevaski and S. O. Nelson, "Moisture content determination in Single Peanut Kernels With a Microwave resonator," Peanut Science, (1993) 20:27.31.]

Microwave moisture sensor (U.S. Pat. No. 4,991,915, issued on Feb. 12, 1991) works on the principle of absorption of the microwave energy into the material. This type of sensor is useful in case of high moisture content as the attenuation characteristics of microstrip are sensitive to the heavy losses in the material under test. U.S. Pat. No. 5,313,167 issued in 1994 teaches coaxial line for introducing microwave energy with the detector coaxial line kept at a distance.

The waveguide cavity measurement technique is associated with the difficulties of loading and unloading of individual kernels and placing them accurately inside the cavity. The number of direct current conductivity and capacitance measurement based moisture sensors available in the market can handle bulk grain samples only where it is impossible to measure the range of moisture contents or dielectric parameters of the grains or materials. They are also affected by the air gaps in the grain samples and conductivities of the grain covers as well as non-uniform shapes. The conductivity based moisture meters need constant pressure to be applied to the bulk under measurements for the validity of look up tables. Hence they are subject to the human errors.

Low frequency techniques are associated with the contributions due to the ionic conductivities of the moist grain and hence are subjected to inherent errors. These type of sensors are based on the power measurement and are totally dependent on the calibration of the materials on the custom made sensor and totally dependent on the dynamic performance of the detector system and its readout system performance.

U.S. Pat. No. 4,408,128 works on the principle that the electric capacity of a sample held between positive and negative electrodes is measured and the value of moisture content thereof is indicated on the basis of the correlation studies in advance between moisture content and electrical characteristic.

Due to the variation in the grain size, a single moisture meter fails to serve the purpose of all cereal products. It is therefore necessary to provide a moisture meter having correlation's calibrated for five respective cereal products according to the type of grain size. The apparent difference in the water content value caused by the difference in the temperature at the time of measurement makes correction by temperature desirable.

A method where a plurality of keys designating the type of sample with programmable EPROM read only memory capable of erasure and rewriting for storing parameters for computation are provided, is also known in the art. The EPROM is fed with the precalibrated values of capacitor voltage and moisture content. The indicator indicates the moisture content in the digital form. However, in this patent it is not clear whether the instrument measures moisture in a single grain or in a bulk of sample, e.g., 100 gm of grains. The description of the actual sensor geometry and dimensions is not drawn or given. The drawbacks associated with this patent specifically relate to the fact that the single type of grain like wheat or rice has variation in the grain size. The capacity is a function of thickness and area and permittivity of the material between the plates. The said instrument does not give effective variation in the capacity with the size and weight of individual grains. If they measure 100 g of grains, air gaps between the grains effect the reading thereby indicating a lower moisture content then the actual true value.

Another U.S. Pat. No. 5,646,537 describes a time domain reflectometry waveguide assembly for measuring the moisture content in a medium and comprises calculating the apparent dielectric constant value of said medium based on a time delay measured in response to said detectable characteristic reference reflection, and correlating the apparent dielectric constant value with data reflecting the moisture content of the medium.

Another U.S. Pat. No. 5,420,517 defines a time domain reflectometry waveguide assembly for measuring the moisture content in a medium.

Microwave moisture sensor (U.S. Pat. No. 4,991,915, issued on Feb. 12, 1991) works on the principle of absorption of the microwave energy into the material. This type of sensor is useful in case of high moisture content as the attenuation characteristics of microstrip are sensitive to the heavy losses in the material under test. These sensors are based on the power measurement and are totally dependent on the calibration of the materials on the custom made sensor and totally dependent on the dynamic performance.

U.S. Pat. No. 5,313,167 issued in 1994 teaches coaxial line for introducing microwave energy with the detector coaxial line kept at a distance.

The waveguide cavity measurement technique is associated with the difficulties of loading and unloading of individual kernels and placing them accurately inside the cavity. The number of direct current conductivity and capacitance measurement based moisture sensors available in the market can handle bulk grain samples only where it is impossible to measure the range of moisture contents or dielectric parameters of the grains or materials. They are also affected by the air gaps in the grain samples and conductivity's of the grain covers as well as non-uniform shapes. The conductivity based moisture meters need constant pressure to be applied to the bulk under measurements for the validity of look up tables. Hence they are subject to the human errors.

Low frequency techniques are associated with the contributions due to the ionic conductivity's of the moist grain and hence are subjected to inherent errors. These type of sensors are based on the power measurement and are totally dependent on the calibration of the materials on the custom made sensor and totally dependent on the dynamic performance of the detector system and its readout system performance.

The sensors which measure moisture in the 100 g of grain samples are incapable of measuring a range of moisture in the grain stock. Mixing of grains containing different moisture contents lead to the degradation of the complete stock. Hence it is important to measure moisture in individual kernels. The same applies to the moisture measurements before harvesting for the estimation of the national or regional yield to predict the national needs for import or export. Similarly moisture measurement of liquid samples such as sugar syrups, milk products, fruits such as grapes, apples, watermelon etc. require determination of precise moisture content.

Moisture measurement in industrial products like rubbers, foams, soaps is a commercially important technique for the quality control. Number of techniques in the market include conductivity, capacitance, frequency shift, time domain and nuclear techniques. Most of these techniques are destructive and demand machining of samples to peculiar geometry of insertion of probes into the material.

The drawbacks of the conventional methods for determination of moisture content hinder the exact determination of the moisture content. The need has therefore been realised for a method and an instrument for determining the moisture content in various samples which overcomes the problems mentioned above. Time domain technique is a powerful measurement tool for the dielectric constant of the sample under test.

SUMMARY OF THE INVENTION

The present invention relates to an instrument for moisture content determination in various samples. The instrument of the present invention uses the measurement of dielectric properties for quantifying the moisture content of samples working in the range of microwave frequencies.

The present invention also relates to a process and instrument for determining moisture content in the solid as well as liquid samples. The samples for which moisture content is to be measured could be grains such as wheat, rice, maize, millet; seeds such as coffee, cotton; pulverised samples such as wheat flour, ground coffee; fruits such as grapes, apples, watermelons; nuts and dry fruits such as almonds, cashews, resins etc.; industrial products such as soaps, soap powders, polymers, rubbers, ceramics; food products such as biscuits, cakes, meat products and other solid and/or liquid samples. More precisely it relates to non-destructive moisture sensing instrument which uses dielectric properties and effective microstrip permittivity for measuring moisture content of samples in Time domain.

Thus the present invention aims to overcome the drawbacks in the existing sensors by providing an accurate, reliable and repeatable, density and volume independent state of art computer aided microwave apparatus for the measurement of dielectric properties and hence moisture in agricultural, food and other insulating industrial products.

Accordingly the present invention relates to an instrument for measurement of moisture content of an article such as grains, pulverised samples, fruits, nuts and dry fruits, industrial and food products, comprising an oscillator, a source of power supply in the microwave range; means for loading and unloading the article; means for providing orientation to the sample; a sensor circuit and a detector for measurement of Q factor and frequency shift of the article.

The invention also defines a process for the measurement of moisture content of an article comprising measuring the resonant frequency and quality factor of a microwave microstrip resonator and calculating the shift in the resonant frequency caused by the change in the effective permittivity of the microstrip structure where the change in the resonant frequency is governed by the relation $$\frac{f_o^2}{f_s^2} = \frac{\varepsilon_{effs}}{\varepsilon_{effo}}$$

DETAILED DESCRIPTION OF THE PRESENT INVENTION

Measuring and monitoring moisture content helps in maintaining the quality and increasing the shelf life of a product. Dielectric constant of pure water lies in the range 75–80 at different frequencies. Dielectric constant of dry soil, grain, food products like biscuits and chocolates as well as rubbers and soap cakes and powders have a much smaller value.

The novel instrument of the present invention is useful in measuring the moisture contents of various commercially important items like grains such as wheat, rice, maize, millet; seeds such as coffee seeds, cotton; pulverized samples such as wheat floor, ground coffee; fruits such as grapes, apples, watermelons; nuts and dry fruits such as cashewnuts, resins etc.; industrial products such as soaps, soap powders, polymers, rubbers, ceramics; food products such as biscuits, cakes, meat products etc.

The object of the present invention is to provide a nondestructive microwave instrument for moisture measurement which obliviates the drawbacks in the existing methods and provide accurate, reliable and repeatable results; which are density and volume independent.

Another embodiment of the present invention also resides in an instrument, process and technique for the measurement of the moisture content of a sample, non destructively without physically probing material and by means of electromagnetic field probe in the vicinity of the stripline, microstripline or coplanar waveguide as an external probing instrument connected to a Time Domain reflectometer. A conventional Time Domain reflectometer is used for the measurement of delay in the reflection from the discontinuity in the characteristic impedance of the probing waveguide In an embodiment of the present invention the microwave source may have frequencies above 1 Ghz in the microwave range.

In another embodiment the functional hybrid microstrip resonator circuit consists microstrip delineated on a ceramic substrate with chrome-gold conductor patterns with sample support structures confirming to the desired orientation In yet another embodiment of the invention the sample can be loaded on the sample holder without disturbing the precalibrated instrument.

In another feature of the present invention the response and recovery time of the sensor is of the order of one second.

The present invention offers nondestructive and relatively faster moisture measurement within solid or liquid samples of any shape or size and in the individual or bulk kernels of nuts, seeds and grains.

The invention also defines a process and instrument for the measurement of effective permittivity of the microstrip, stripline or coplanar waveguide embedded with dielectric overlay or cover. The effective permittivity of any of the waveguide probes defined above is measured by means of measuring change in the delay, change in the reflection coefficient and/or change in the characteristic impedance due to the presence of sample as an overlay or dielectric cover over the microstrip, stripline or coplanar waveguide conducting probing instrument. The change in the effective permittivity is governed by the relation $$t_s^2/t_o = \varepsilon_{effs}/\varepsilon_{effo}$$

where suffices 'o' and 's' indicate time delay (t) and effective permittivity ($\varepsilon_{eff}$) without and with sample grain as an overlay.

The present time domain instrument is applicable for the measurement of moisture in materials of any size and shape with at least one dimension of the order or greater than 3 mm. A microstrip and coplanar waveguide probe is used for the nondestructive measurement of moisture. The time domain reflectometer generating pulse inputs of picosecond resolution is connected to any one or multiple probes by means of a coaxial cable of matching impedance described above, The choice of the probe depends upon the geometry and the composition of the material. The material under test is kept as an overlay on the microstrip probe. The change in the effective permittivity of the microstrip/coplanar waveguide probe is calibrated against moisture with optional electromagnetic software and a dedicated microcontroller or a computer. The calibration data is stored in the computer to give a directly correlated moisture percentage on the dedicated portable laptop or a fixed computer.

The object of the present invention is to provide nondestructive, accurate, fast, reliable and repeatable moisture measurement which eliminates the drawbacks of existing instruments processes and methods.

In an embodiment of the present invention the Time domain Reflectometer may have a pulse or step output containing frequency components between 0–20 Ghz or less with a coaxial cable carrying the step or pulse output of the Time Domain Reflectometer.

According to the present invention there is provided a microwave functional hybrid microstrip circuit, source of the microwave power and the detector in the instrument for measuring the moisture content. The product to be tested is kept in the transverse vicinity of the circuit causing changes in the properties of the medium of propagated of microwave energy. The changes in the output power in terms of resonant frequency and quality factor caused by the presence of the product under test are correlated to moisture contents of the sample. The analytical and experimental study of the instrument has indicated that the samples thicker than 0.8–1.2 mm and wider than 2.6 to 3.5 mm can be tested independent of their dimensions and mass.

A multilayer microstrip functional hybrid integrated circuit with dielectric overlay is used in the present instrument in the form of a sample holder consisting of a microstrip resonator with the support structure to confirm to the desired orientation. The use of a microstrip resonant frequency and Quality factor is a novel concept in the determination of moisture content. Ring resonator is generally used for the purpose of the present invention.

Microstrip, a miniature and planar microwave component has been used in the present invention as a resonant cavity sensor to offer non destructive and relatively faster moisture measurement within individual kernels of samples. The main principle behind the instrument of the present invention is that the effective permittivity, characteristic impedance and losses in a single microstrip vary due to the presence of a dielectric cover on a microstrip. At the same time resonant frequency and transmission and quality factors of microstrip resonators change due to the change in the basic microwave properties due to partial or full overlays on it. The change in the resonant frequency is governed by the relation $$\frac{f_o^2}{f_s^2} = \frac{\varepsilon_{\mathit{effs}}}{\varepsilon_{\mathit{effo}}}$$

where suffices 'o' and 's' indicate resonant frequency (f) and effective permittivity ($\epsilon_{\mathit{eff}}$) without and with sample grain as an overlay on the ring resonator respectively.

$$\delta f_o = f(\epsilon_{\mathit{eff}})$$

and $$\delta Q = f(\epsilon'_{rs} \epsilon''_{rs})$$

where $\epsilon_{rs}$ is the relative permittivity of the grain and $\epsilon'$ and $\epsilon''$ indicate real and imaginary parts of the complex permittivity $\epsilon$. The dielectric constant of the dry samples is much lesser as compared to the dielectric constant of water. Resonant frequency of the ring resonator is highly sensitive to the moisture level of the wheat grain due to the difference in the relative permittivities of dry samples and water. Whereas Q factor is sensitive to both $\epsilon'$ and $\epsilon''$ of the overlay material as conductor loss of the microstrip with cover is also subject to the changes in the inductance per unit length of the microstrip.

The change of the moisture content of wheat grain causes change in the effective permittivity and hence the resonant frequency. The change in the complex permittivity causes change in the Q factor. Variation of the moisture content is calibrated against frequency as well as Q factor.

The resonant frequency of the microstrip resonator is highly sensitive to the presence of an overlay sample. Q factor decreases by about 48–53% when the moisture content increases by 30–41% whereas when the moisture content decreases by about 1–6% the Q factor increases by 10–20%. Therefore the Q factor and the moisture content have been known to be inversely proportional to each other. The lowest sensitivity has been observed in 0° orientation and 90° orientation gives the highest sensitivity.

FIG. 2 shows the variation in the Q factor for different weight groups and four different orientations. FIG. 3 shows Q factor variation for four different weight groups at 90° orientation. FIG. 4 shows the variation of resonant frequency with percentage moisture content for a particular weight group with different orientations. FIG. 5 shows variation of resonant frequency with percentage moisture for four different weight groups at 90° orientation.

The results indicate that the Q factor measurements are weight independent as the Q factors lie in the same range even though the changes in the weight of the kernels are 45%. The sensitivity factor dQ/dM varies for different orientations where M indicates percentage moisture.

Therefore the Q factor and frequency shift measurements of a microstrip ring resonator are used successfully to perform highly sensitive moisture measurements independent of the volume and weight of the individual grain. The resolution of less than 1% has been obtained in the very wide range of moisture percentage.

In another embodiment of the present invention regarding the time domain instrument the functional hybrid microwave transmission line resonator circuit consists of a microstrip, stripline or coplanar waveguide resonator could be a direct coupled either open ended or short circuited with a sample holder to hold sample in a particular position covering the entire area of the substrate and extending beyond the end of the conductor and substrate of a smaller size than that of the length of the resonator or a microstrip rectangular patch with a sample holder to hold sample under test in a particular position covering the entire area of the substrate and extending beyond the end of the conductor and substrate of a smaller size than that of the length of the patch.

In another embodiment of the present invention the functional hybrid through microwave transmission line circuit consists of a microstrip, stripline or coplanar waveguide.

In yet another embodiment of the present invention the functional hybrid through microwave transmission line on a resonator circuit consists of either microstrip, stripline or coplanar waveguide delineated on glass, ceramic, polymer or semiconductor substrate with chrome gold or copper gold conductor pattern with optional thin dielectric coating also with optional sample holding structure.

In another embodiment of the present invention a process and technique to measure the effective permittivity of a sample as an overlay without disturbing the calibration of the instrument without the sample hence avoiding error due to the connector repeatability is defined.

In another feature of the present invention the process and technique to measure the effective permittivity of a sample as an overlay has been defines where the response and recovery time of the sensor instrument is of the order of a fraction of a second.

The process for the measurement of the moisture content comprises of steps of calibrating the Time domain reflectometer, selecting probe dimensions and type, marking start of the probe by placing the marker on the Time Domain Reflectometer screen, placing the sample under test on the probe or place the probe on the sample so that the microstrip conductor is in contact with the material externally or with an adjusted air gap without physical contact and analysing the data with the computer or look up tables and get moisture percentage.

The process for the measurement of moisture content of a liquid or a solid sample using a time domain reflectometry assembly, comprises calibrating a time domain reflectometer;
selecting microstripline, stripline or coplanar waveguide probe suitable for the type of sample;
connecting a coaxial cable to the probe;
positioning the sample on a sample holder;
transmitting a pulse signal of the kind used in time domain reflectometry through the coaxial cable;
commencing a measurement of time delay in response to the characteristic reference reflection;
calculating effective permittivity based on the time delay and calibrating effective permittivity against moisture with optional electromagnetic software and a dedicated microcontroller or a computer or with calibration graphs and tables.

The time domain reflectometer as already mentioned generates the pulse of picosecond duration. The said sample is placed on a microstrip patch covering the entire area of the substrate and extending beyond the end of the conductor and substrate or substrate of smaller size than that of the length of the said resonator.

The instrument of the present invention optionally comprises spacer block placed over the said sample for putting pressure on the sample. This spacer block therefore enables removing the air gap present. The presence of air gap causes an error in the measurement of moisture content which could vary the results by as big as 10% error. Therefore spacer blocks of effective permittivity of approximately 1 can be defined.

A probe length may be varied depending upon the material, dielectric constant of the material and moisture levels to be measured.

In another optional feature of the present feature of the present invention the microcontroller or a dedicated computer calculates effective permittivity and the moisture content of the sample or medium under test or calibration graphs and tables provide correlation between the measured data on time delay for pulse step or step input signal to return or reflection coefficient or characteristic impedance of the sensor probe.

Figure 6:
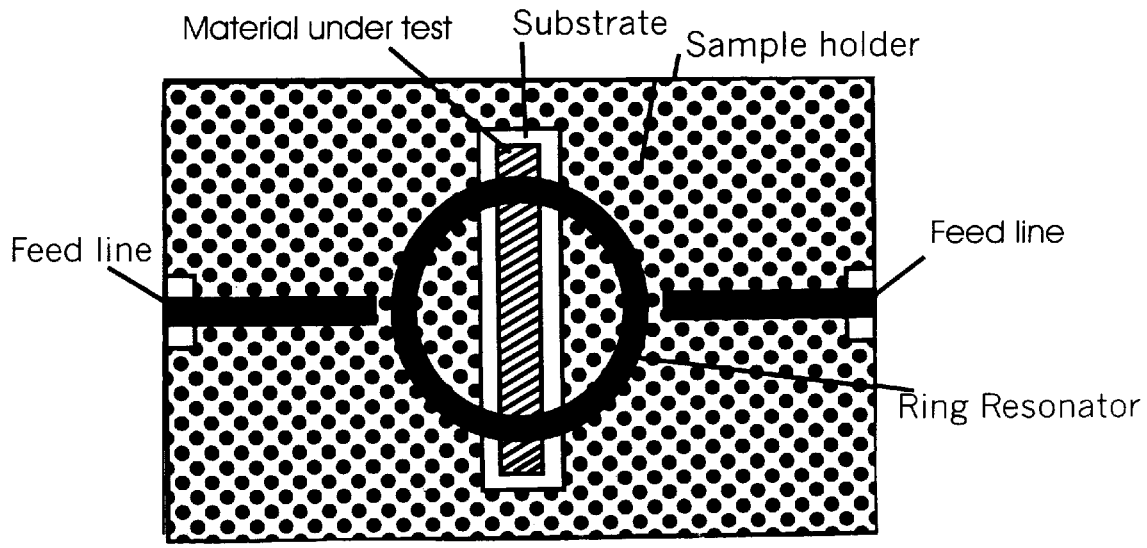

According to the present invention therefore there is provided a functional microwave functional hybrid microstrip or stripline or a coplanar waveguide circuit, a voltage step generator and an instrument sampling the returned pulse. The presence of sample causes a change in the effective permittivity of the microstrip, stripline or a coplanar waveguide structure. The change in effective permittivity is therefore calibrated and the dielectric constant evaluated. To understand the present invention clearly a set of drawings are submitted wherein FIG. 1 shows the arrangement of the components of the instrument for measuring moisture content of the sample wherein the microwave source and functional microstrip sensor circuit and detector are arranged in a particular manner. FIG. 2 shows the variation in the Q factor for different weight groups and four orientations while FIG. 3 represents Q factor variation for four different weight groups at 90° orientation. FIG. 4 shows the variation of resonant frequency with percentage moisture content for a particular weight group with different orientations and FIG. 5 shows variation of resonant frequency with percentage moisture for four different weight groups at 90° orientation. FIG. 6 shows the ring resonator with material under test.

Figure 7:
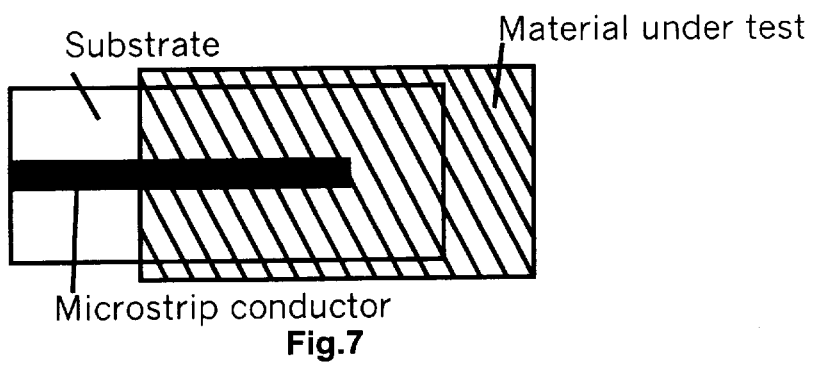
Figure 8:
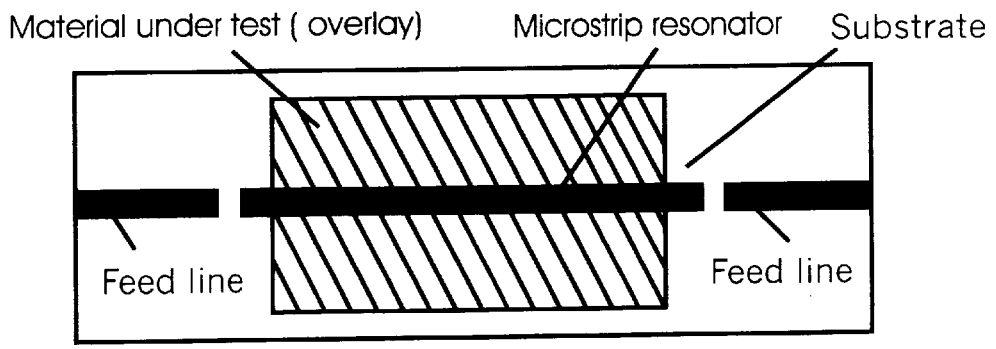
Figure 8:
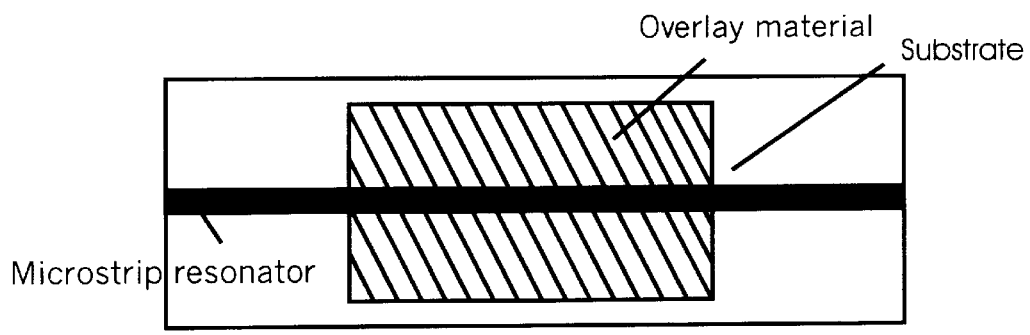
Figure 9:
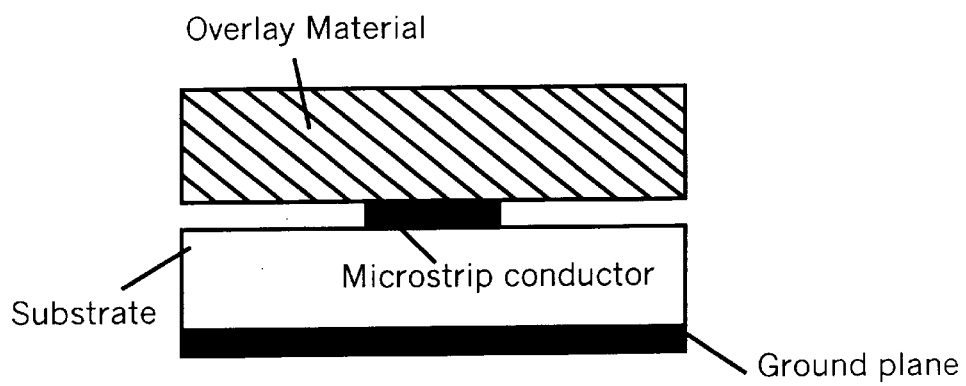
Figure 10:
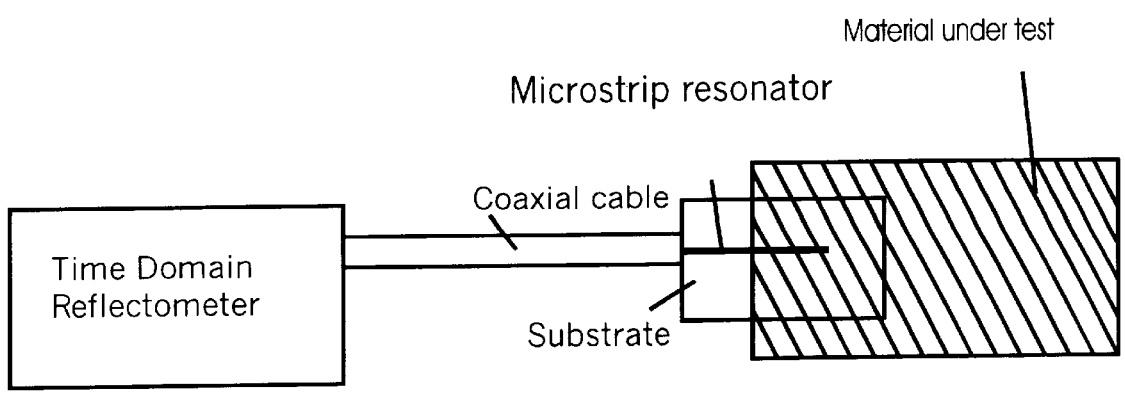
Figure 11:
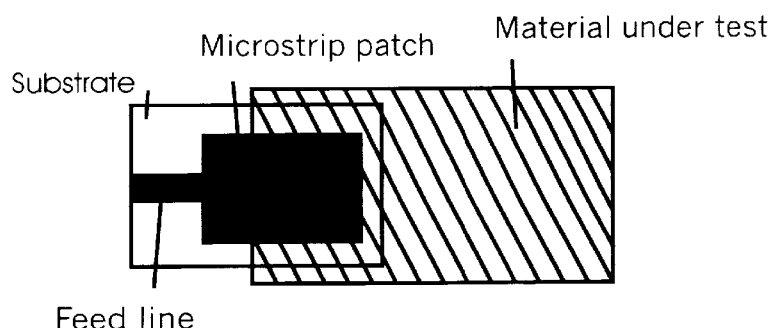
Figure 12:
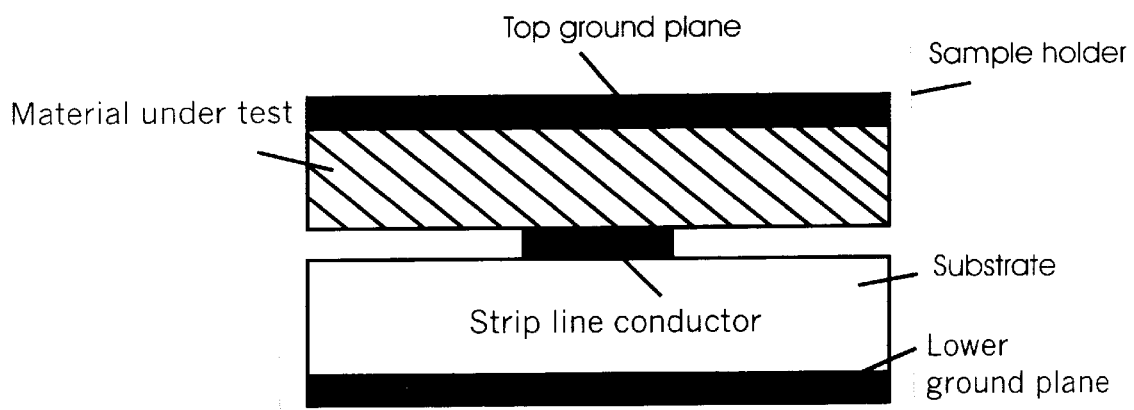
Figure 13:
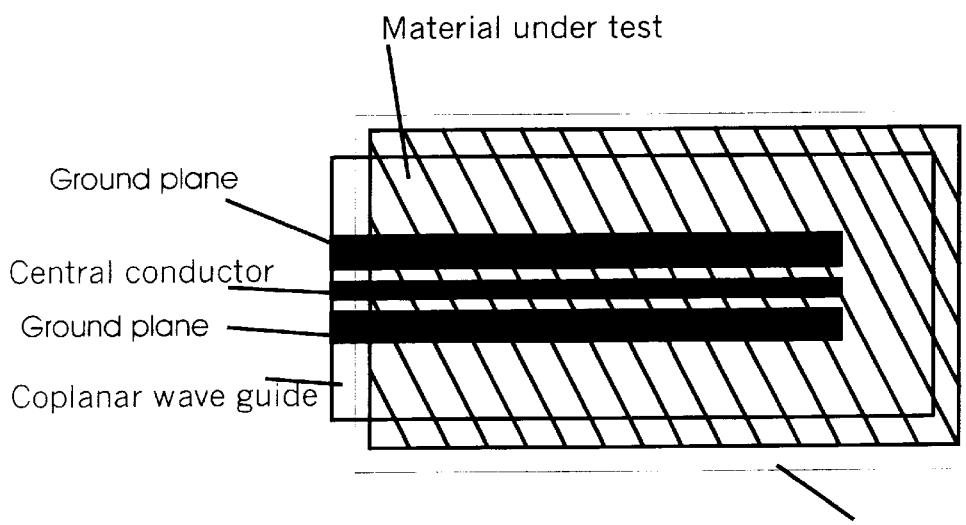

FIG. 7 shows quarter wavelength microstrip probe for moisture measurement. FIG. 8(a) depicts half wavelength microstrip probe for moisture measurement and FIG. 8(b) shows a microstrip line probe for moisture measurement. FIG. 9 shows cross section of microstrip probe for moisture measurement while FIG. 10 shows arrangement of components and the time domain reflectometer. FIG. 11 shows microstrip patch for moisture measurement and FIG. 12 depicts stripline probe for moisture measurement. FIG. 13 shows coplanar waveguide probe for moisture measurement. FIG. 14 shows time domain measurement of electrical length on HP8510C.

The present invention can be clearly understood with the help of the examples. While the specification concludes with claims particularly pointing out and distinctly claiming the present invention, it is believed the present invention will be better understood from the following description in conjunction with the accompanying drawings.

EXAMPLES

About 100 wheat grains of a high quality "Lokawan" variety grown in Gujarat state of India are taken. These are classified into four weight groups:

(a) 0.045±0.005 gm (b) 0.055±0.005 gm (c) 0.065±0.005 gm (d) 0.075±0.005 gm

The individual grains are kept on a ring at different orientations viz. 0°, 45°–45° and 90°. The change in the resonant frequency and change in the quality factor of the ring are recorded while varying the moisture levels from 15% to 40% by oven drying and soaking in water while considering the starting level as reference level. Q factor of the lowest weight group viz ±0.045 decreases by 51% when the moisture content of the grain is increases by 36% whereas as the moisture content decreases by 4% the Q factor increases by 15%. The lowest sensitivity is observed at 0° orientation and 90° orientation gives the highest sensitivity. The results are shown in the FIGS. 2–5.

The results clearly indicate that the Q factor measurements are weight independent as the Q factor lies in the same range even though the changes in the weight of the kernels are 45%.

What is claimed is:

1. A process for the measurement of moisture content of an article selected from the group consisting essentially of grains, pulverized samples, fruits, nuts, dry fruits, and industrial and food products, comprising the steps of:

selecting a multilayer microstrip integrated hybrid circuit from the group consisting of a microstrip with dielectric overlay, an asymmetric inhomogeneous Stripline, and a coplanar waveguide with dielectric overlay;

precalibrating a pulse generator and a time domain reflectometer;

connecting a pulse generating source to an input end of the multilayer microstrip integrated hybrid circuit;

connecting an output end of the multilayer microstrip integrated hybrid circuit to a detector in a transmission mode;

calibrating the time domain reflectometer and recording time of propagation through the multilayer microstrip integrated hybrid circuit;

placing the sample over the multilayer microstrip integrated circuit in a sample holder;

measuring time delay using the time domain reflectometer in response to a characteristic reference reflection obtained in the step of calibrating the time domain reflectometer;

calculating effective permittivity based on a group of parameters of time domain reflectometer, time delay, reflection coefficient, and characteristic impedance of the multilayer microstrip integrated hybrid circuit; and calibrating effective permittivity against moisture.

2. The process of claim 1, wherein the step of calibrating effective permittivity against moisture is accomplished using electromagnetic software.

3. The process of claim 1, wherein the step of calibrating effective permittivity against moisture is accomplished using a dedicated microcontroller.

* * * * *

UNITED STATES PATENT AND TRADEMARK OFFICE
CERTIFICATE OF CORRECTION

PATENT NO. : 6,204,670 B1
DATED : March 20, 2001
INVENTOR(S) : Kalpana K. Joshi et al.

It is certified that error appears in the above-identified patent and that said Letters Patent is hereby corrected as shown below:

<u>Column 7,</u>
Line 21, should be -- $\Delta f_o = f(\epsilon_{eff})$ -- instead of "$\delta f_o = f(\epsilon_{eff})$".
Line 26, should be -- $\Delta Q = f(\epsilon'_{rs} \epsilon''_{rs})$ -- instead of "$\delta Q = f(\epsilon'_{rs} \epsilon''_{rs})$".

Signed and Sealed this

Seventeenth Day of September, 2002

Attest:

JAMES E. ROGAN
Attesting Officer        Director of the United States Patent and Trademark Office

UNITED STATES PATENT AND TRADEMARK OFFICE
CERTIFICATE OF CORRECTION

PATENT NO. : 6,204,670 B1 Page 1 of 1
DATED : March 20, 2001
INVENTOR(S) : Kalpana K. Joshi et al.

It is certified that error appears in the above-identified patent and that said Letters Patent is hereby corrected as shown below:

Column 7,
Line 21, should be -- $\Delta f_o = f(\mathcal{C}_{eff})$ -- instead of "$\delta f_o = f(\mathcal{C}_{eff})$".
Line 26, should be -- $\Delta Q = f(\mathcal{C}'_{rs}\mathcal{C}''_{rs})$ -- instead of "$\delta Q = f(\mathcal{C}'_{rs}\mathcal{C}''_{rs})$".

Signed and Sealed this

Fifteenth Day of October, 2002

Attest:

JAMES E. ROGAN
Attesting Officer           Director of the United States Patent and Trademark Office